United States Patent
Yamamoto

(10) Patent No.: US 6,969,387 B2
(45) Date of Patent: Nov. 29, 2005

(54) LASER HAND-PIECE AND LASER TREATMENT APPARATUS PROVIDED WITH THE HAND-PIECE

(75) Inventor: Mitsuo Yamamoto, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 220 days.

(21) Appl. No.: 10/126,672

(22) Filed: Apr. 22, 2002

(65) Prior Publication Data

US 2002/0161359 A1 Oct. 31, 2002

(30) Foreign Application Priority Data

Apr. 25, 2001 (JP) .............................. 2001-127204

(51) Int. Cl.[7] .............................................. A61B 18/20
(52) U.S. Cl. ........................... 606/13; 606/10; 606/17; 606/19
(58) Field of Search ............. 606/1, 10–19; 607/88–91

(56) References Cited

U.S. PATENT DOCUMENTS

| | | | |
|---|---|---|---|
| 4,069,823 A | * | 1/1978 | Isakov et al. ................. 606/19 |
| 4,865,029 A | * | 9/1989 | Pankratov et al. ............. 606/4 |
| 5,150,704 A | * | 9/1992 | Tatebayashi et al. .......... 606/19 |
| 5,474,449 A | * | 12/1995 | Loge et al. .................... 606/19 |
| 6,129,721 A | | 10/2000 | Kataoka et al. |

FOREIGN PATENT DOCUMENTS

JP 10-328197 12/1998

* cited by examiner

*Primary Examiner*—David M. Shay
(74) *Attorney, Agent, or Firm*—Oliff & Berridge, PLC

(57) ABSTRACT

A laser hand-piece for irradiating a treatment laser beam to a part to be treated is disclosed. The laser hand-piece includes: a main body including an end portion with a bend and a grip portion to be held by an operator's hand, the end and grip portions each having an inner optical path communicating with each other for guiding the laser beam; a laser guiding pipe pivotally mounted on the end portion of the main body and provided with an inner optical path communicating with the inner optical path of the end portion to guide the laser beam, an opening, and a mirror for discharging the laser beam having been guided through the inner optical path to outside through the opening; a rotary knob rotatably attached to the grip portion; and a rotation transmitting mechanism, disposed between the rotary knob and the laser guiding pipe, for transmitting rotation of the rotary knob to the laser guiding pipe to change a laser irradiation direction.

8 Claims, 4 Drawing Sheets

LASER HAND-PIECE AND LASER TREATMENT APPARATUS PROVIDED WITH THE HAND-PIECE

BACKGROUND OF THE INVENTION

1. Field of the Invention

The present invention relates to a laser hand-piece for performing treatment on a part of a patient to be treated by irradiating the treatment part with a laser beam, and more particularly to a hand-piece usable for treatment in a hospital's department or clinic of otolaryngology and a laser treatment apparatus provided with the hand-piece.

2. Description of Related Art

Heretofore, there has been known a laser treatment apparatus using a $CO_2$ laser beam (a carbon dioxide laser beam) with a wavelength in an infrared region in order to treat nasal allergy, etc. In the laser treatment for nose, a hand-piece provided with a pipe (a laser guiding pipe) in which a mirror for reflecting the laser beam is mounted at a tip is used to irradiate the laser beam into a nostril of a patient. This hand-piece has been materialized in some shapes; one type has a straight shape from a grip part to the pipe, and another has a bent end like a sign "<" to which the pipe is attached for the purpose of improving visibility of the inside of the nose.

Meanwhile, the hand-piece of the straight type, if rotated itself, relatively simply allows a change of a laser irradiation direction according to right and left nostrils and positions (angles) of parts to be irradiated. The hand-piece of the bent type, on the other hand, becomes difficult to handle if it is rotated itself. Accordingly, this type has been arranged to change the laser irradiation direction by interchanging the pipes with mirror reflection surfaces for left and right nostrils individually, alternatively, by rotating the pipe by tightening or loosing of a mounting screw provided in the end of the hand-piece.

The interchange of the pipes or the rotation of the pipe of the hand-piece with the bent type, however, needs to be conducted by operator's both hands during treatment, which involves much time and effort. Specifically, the operator usually holds the hand-piece by one hand and, by the other hand, an instrument such as a rhinoscope or an endoscope fiber for expanding the nostril. Thus the interchange of the pipes or the rotation of the pipe needing operator's both hands would be troublesome.

SUMMARY OF THE INVENTION

The present invention has been made in view of the above circumstances and has an object to overcome the above problems and to provide a laser hand-piece capable of changing a laser irradiation direction by operator's one hand without troublesomeness even during treatment, and a laser treatment apparatus provided with the hand-piece.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser hand-piece for irradiating a treatment laser beam to a part to be treated, including: a main body including an end portion with a bend and a grip portion to be held by an operator's hand, the end and grip portions each having an inner optical path communicating with each other for guiding the laser beam; a laser guiding pipe pivotally mounted on the end portion of the main body and provided with an inner optical path communicating with the inner optical path of the end portion to guide the laser beam, an opening, and a mirror for discharging the laser beam having been guided through the inner optical path to outside through the opening; a rotary knob rotatably attached to the grip portion; and a rotation transmitting mechanism, disposed between the rotary knob and the laser guiding pipe, for transmitting rotation of the rotary knob to the laser guiding pipe to change a laser irradiation direction.

According to another aspect of the present invention, there is provided a laser treatment apparatus including the above-mentioned laser hand-piece.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
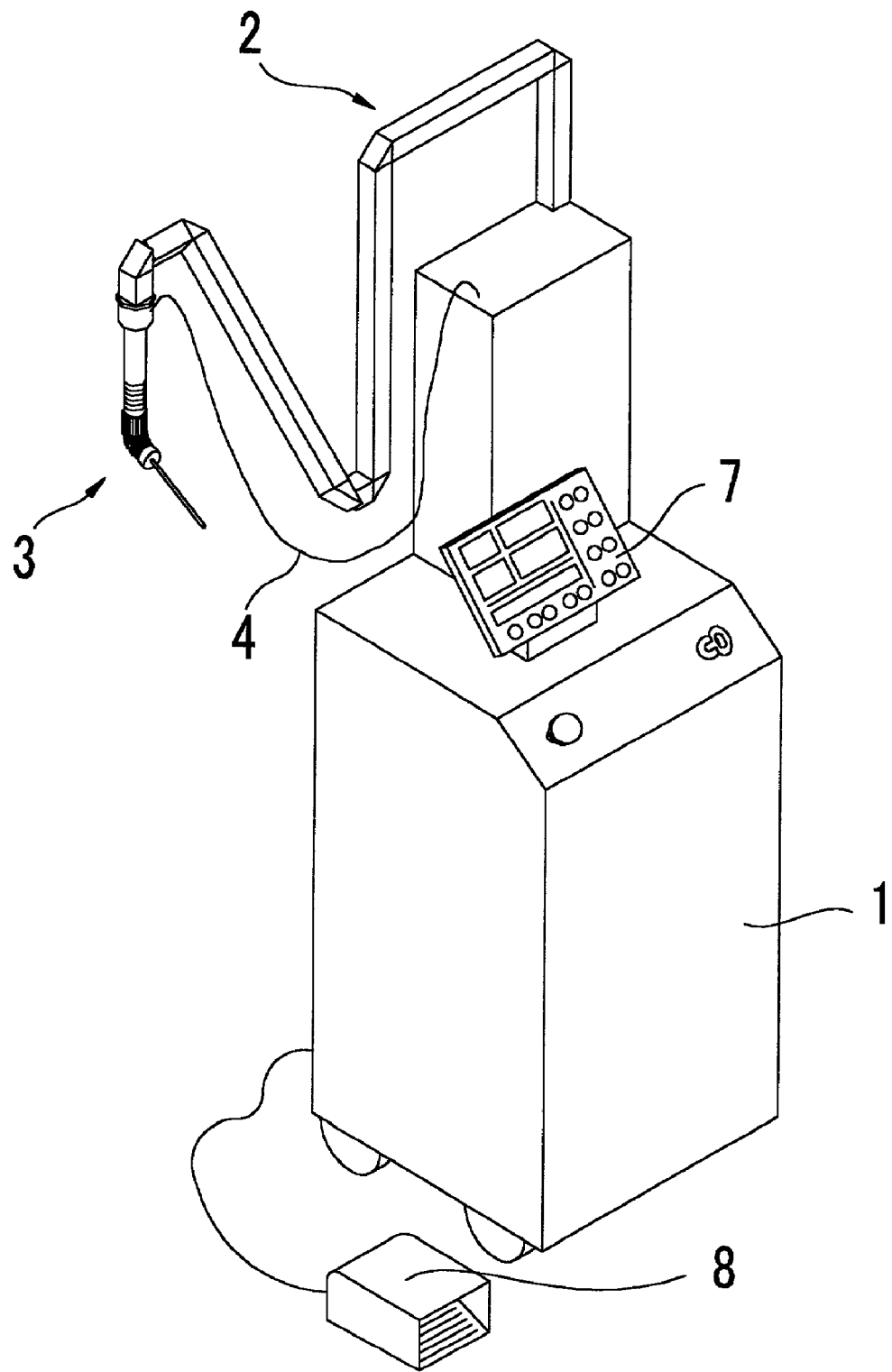
FIG. 1 is a schematic perspective view of a laser treatment apparatus in an embodiment according to the present invention.
Figure 2:
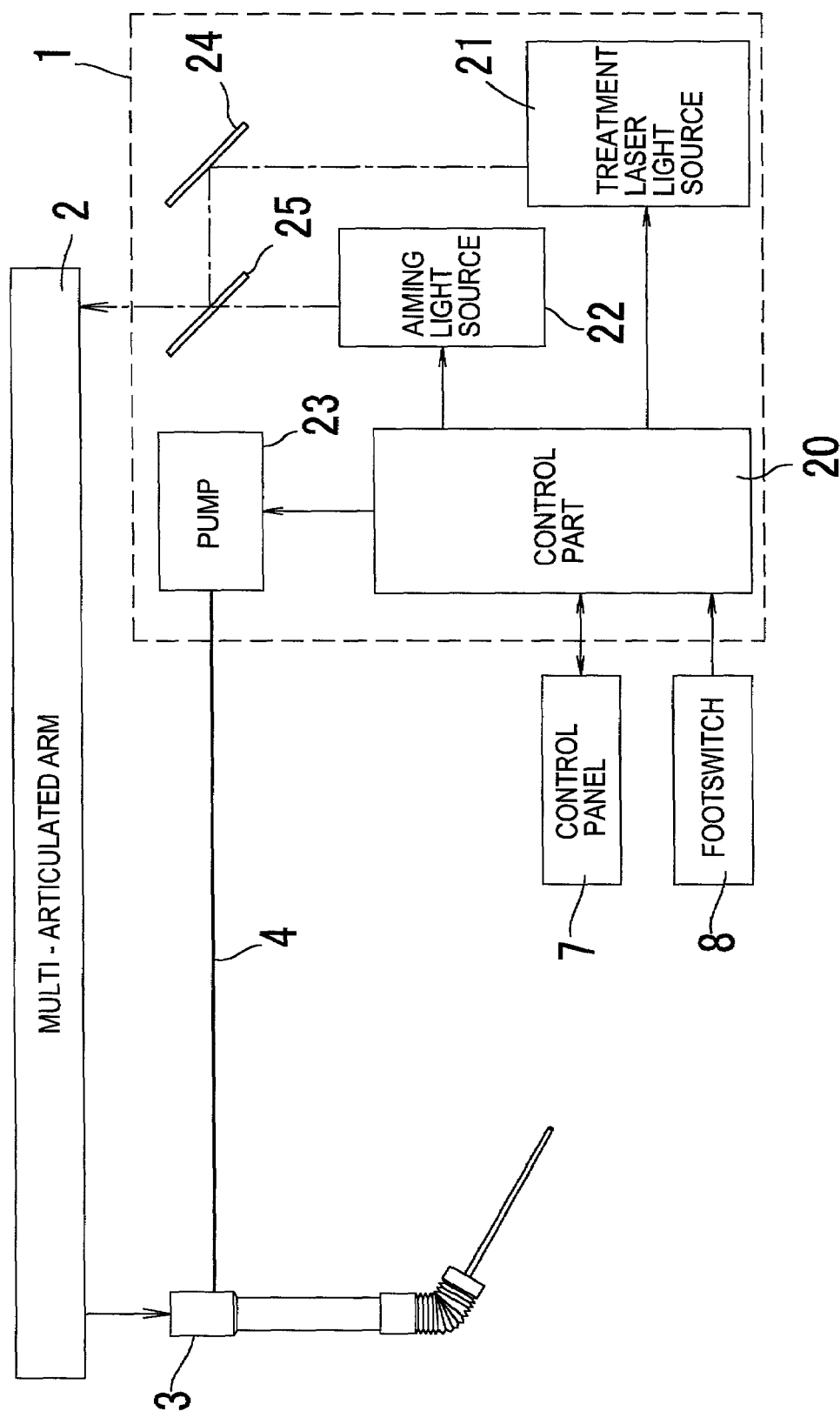
FIG. 2 is a block diagram schematically showing a main structure including a control system and an optical system in the laser treatment apparatus.

A detailed description of a preferred embodiment of a hand-piece and a laser treatment apparatus embodying the present invention will now be given referring to the accompanying drawings. FIG. 1 is a schematic perspective view of the laser treatment apparatus. FIG. 2 is a block diagram schematically showing a main structure including a control system and an optical system in the apparatus.

Numeral 1 denotes a main unit of the laser apparatus, which is internally provided with a control part 20, a laser light source 21 for treatment, a light source 22 for aiming, a light delivery optical system, and others. In the present embodiment, the light source 21 is a $CO_2$ laser source which emits an infrared laser beam to be used as a treatment laser beam, and the light source 22 is a laser diode which emits visible red laser beam to be used as an aiming laser beam.

Numeral 2 is a multi-articulated arm and 3 is a hand-piece. Numeral 7 is a control panel for input of various setting conditions including a laser irradiation condition. Numeral 8 is a footswitch for generating a trigger signal (a laser irradiation command signal) when depressed. Numeral 23 is a pump for supplying air to the hand-piece 3. Numeral 4 is a tube for supplying the air from the pump 23 to the hand-piece 3.

The arm 2 is structured of several rigid pipes flexibly joined one each to another by joints to allow an operator to freely move the hand-piece 3. In the joints of the arm 2, mirrors are disposed individually to guide a treatment laser beam and an aiming laser beam made coaxial with each other by mirrors 24 and 25 in the main unit 1 into the hand-piece 3 through the arm 2.

Figure 3:
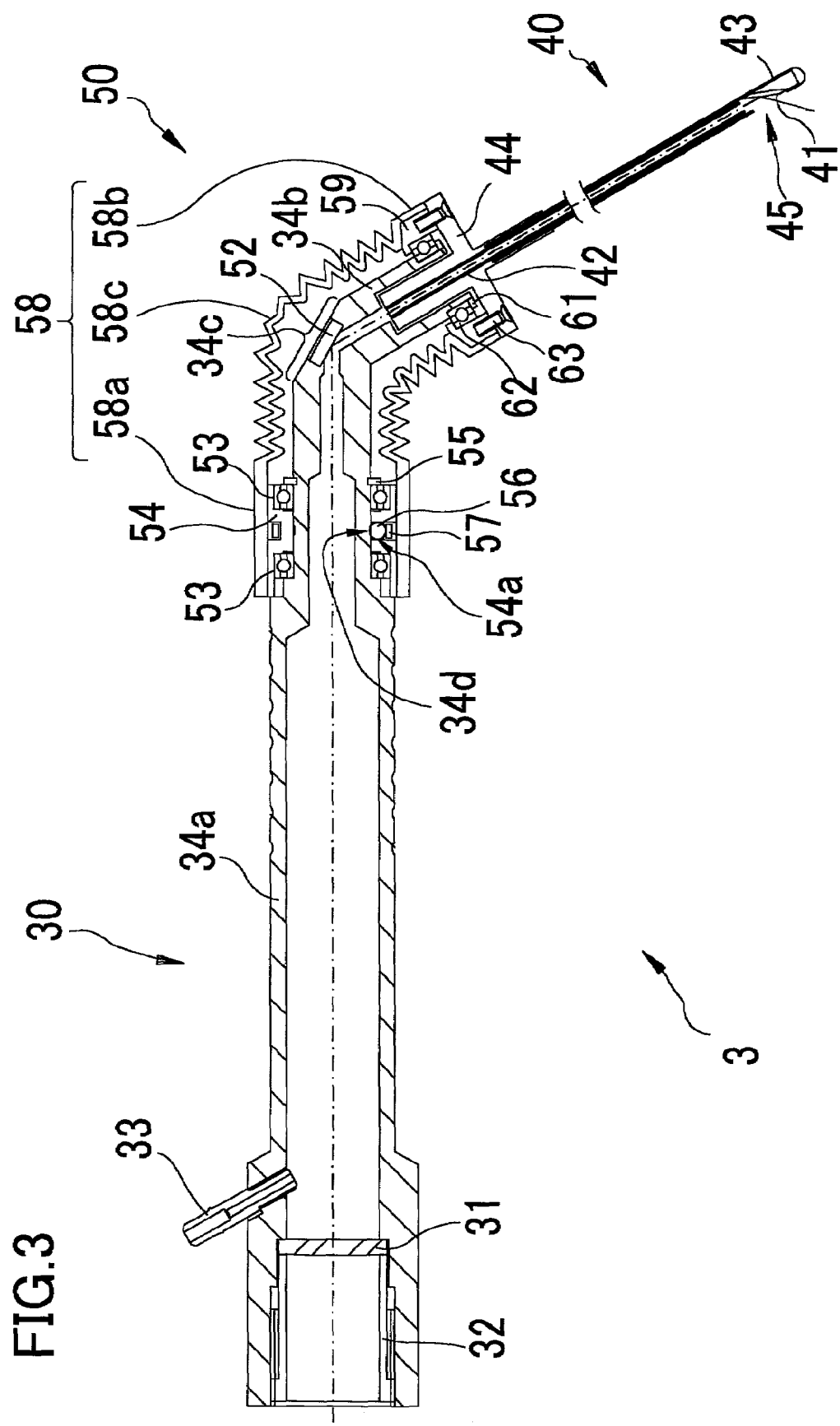
FIG. 3 is a schematic structural view of a hand-piece provided in the apparatus.
Figure 4:
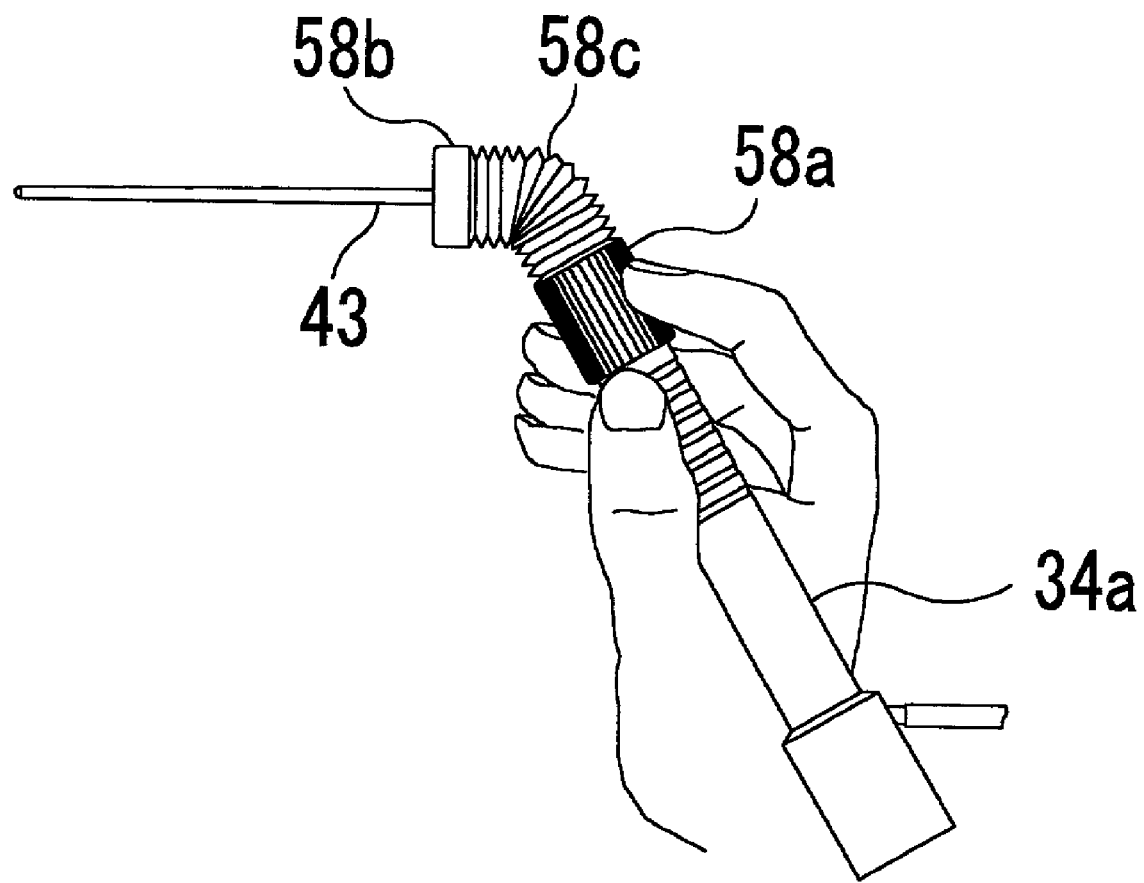
FIG. 4 is an explanatory view showing how the hand-piece is manually held.

FIG. 3 is a schematic structural view of the hand-piece 3. The hand-piece 3 is basically constructed of a main body 30, a pipe member 40 which is inserted in the patient's nostril, and a rotation transmitting mechanism 50 for rotating the pipe member 40.

The pipe member 40 includes a pipe 43 formed near its tip with an opening 45, a rotary base 44 supporting the rear end of the pipe 43, a glass pipe 42 inserted in the pipe 43, providing an optical path for guiding a laser beam, and a mirror 41 disposed in the pipe 43 at a position corresponding to the opening 45. The mirror 41 is used to reflect the laser beam guided through the glass pipe 42 to the outside through the opening 45. The glass pipe 42 serves to efficiently guide the laser beam and to insulate the heat liberated by the laser beam.

The main body 30 of the hand-piece 3 includes a straight extending grip portion 34a which is held by the operator and a bent end portion 34b. Each of the grip portion 34a and the end portion 34b is hollow to configure an inner optical path for guiding a laser beam. Inside a rear end of the grip portion 34a, a condensing lens 31 is fixedly held by a lens holder 32. A mirror 52 is fixed in a bend 34c of the end portion 34a in order to reflect the laser beam toward the pipe member 40.

To the end portion 34b, the pipe member 40 is attached pivotally about its axis. The rotation transmitting mechanism 50 includes a rotation transmitting member 58 provided covering the end portion 34b and part of the grip portion 34a. The rotation transmitting member 58 is entirely made of hard rubber, provided with a center portion 58c of a bellows type capable of flexibly bending. In a front end portion 58b extending over the end portion 34b on the pipe member 40 side, a metallic mounting ring 59 is fitted. A bearing 62 is attached to the end portion 34b on the pipe member 40 side by a bearing retainer 61. The mounting ring 59 is fitted on the outer periphery of the bearing 62. The rotary base 44 of the pipe member 40 is secured to the ring 59 by screws 63. The pipe member 40 is thus rotatable with respect to the end portion 34b.

The portion of the rotation transmitting member 58 extending to the grip portion 34 side forms a rotary knob 58a which is rotated by operator's fingers. Two bearings 53 are mounted between the rotary knob 58a and the grip portion 34a. A rotary ring 54 is attached to the outside of the bearings 53 so that an axially center portion of the ring 54 is sandwiched between the two bearings 53. The rotary knob 58a is fitted on the periphery of the rotary ring 54. Numeral 55 is a bearing retainer for fixing the bearings 53 in place. A steel ball 56 is received in a hole 54a of the rotary ring 54 and pressed toward a center axis of the rotary ring 54 by a ring spring 57 contact with the periphery of the ball 56. The grip portion 34a is formed with eight depressions 34d disposed at 45° intervals on the periphery of the grip portion 34a which contacts the ball 56. Each depression 34d and the ball 56 pressed toward the center axis of the ring 54 constitute a click mechanism for stopping rotation of the rotary ring 54, thus locking the ring 54 at each predetermined rotational position corresponding to the position of each depression 34d.

With the above structure, when the operator turns the rotary knob 58a about the axis of the grip portion 34a by the fingers of the hand holding the grip portion 34a, the rotation of the knob 58a is transmitted to the pipe member 40 through the rotation transmitting member 58. This causes the rotation of the pipe 43 to change the angle of the mirror 41 which reflects the laser beam to the outside, thereby changing a laser irradiation direction.

By unfastening of the screws 63, the pipe member 40 can be removed from the front end portion 58b of the rotation transmitting member 58. The pipe 43 may be replaced with a selected one from various types of pipes; for example, a pipe having a different length, another pipe having no mirror 41, etc.

A nipple 33 for taking air in from the pump 23 is fixed in the grip portion 34a near its rear end. The air taken in through the nipple 33 is guided through the main body 30 and the pipe member 40 and discharged to the outside through the opening 45 formed in the pipe 43 near its end. The air serves to prevent the mirror 41 from getting soiled and also cool the inside of the hand-piece 3 against the heat generated by the laser beam.

The operation of the apparatus having the above structure is explained below. At first the operator operates switches on the control panel 7 to set laser irradiation conditions such as laser output and pulse irradiation time intervals. Simultaneously, the operator turns on a switch not shown to actuate the pump 23, thereby supplying air to the hand-piece 3.

The operator holds the hand-piece 3 with his one hand gripping the grip portion 34a while expands the nostril of the patient by means of a rhinoscope or the like held in the other hand and inserts the tip portion of the pipe 43 in the nostril expanded. While peeping into the nostril, the operator adjusts the position of the pipe 43 inserted in the nostril so that the aiming beam impinges on an affected part to be treated. If attempting to irradiate a back or front portion in the nostril, the operator is required only to move the hand-piece 3 itself backward or forward in the axial direction of the pipe 43. To change the laser irradiation direction rightward or leftward in the nostril, the operator, holding the grip portion 34a by one hand, turns the rotary knob 58a about the axis of the grip portion 34a by the fingers of the hand. The turning of the rotary knob 58a is transmitted to the pipe member 40 through the rotation transmitting member 58, thereby turning the pipe 43 about its axis. The pipe member 40 is then locked at a predetermined rotational position by the click mechanism provided between the rotary knob 58a and the grip portion 34a to prevent further turning thereof. Although the click positions for preventing turning are arranged at 45° intervals on the periphery of the grip portion 34a, a finer adjustment in angle can be achieved by control of the wrist of the operator.

After completion of the positional adjustment for laser irradiation, the operator depresses the footswitch 8 to irradiate the treatment laser beam. The treatment laser beam emitted from the light source 21 is delivered to the hand-piece 3 through the arm 2. The laser beam passes through the condensing lens 31 and is reflected by the mirror 52 and the mirror 41 in turn. The reflected laser beam is emitted to outside through the opening 45 to irradiate the affected part.

At execution of the laser irradiation in the other nostril, as with the above case, the operator is also required only to turn the rotary knob 58a by the fingers of the hand holding the hand-piece 3 to turn the pipe 43. Thus the laser irradiation direction can easily be changed.

The present invention may be embodied in other specific forms without departing from the spirit or essential characteristics thereof. In the above embodiment, the rotation transmitting member 58 integrally formed with the rotary knob 58a is made from hard rubber. Alternatively, the flexibly bendable portion 58c may be formed of a coil spring.

According to the above structure of the invention, the laser irradiation direction can be changed by operator's one hand without troublesomeness even during treatment.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser hand-piece of a bent-type, for irradiating a treatment laser beam to a part to be treated, comprising:
    a main body including a bent end portion and a grip portion to be held by an operator's hand, the end and grip portions each having an inner optical path communicating with each other for guiding the laser beam;
    a laser guiding pipe pivotably mounted on the end portion of the main body and provided with an inner optical path communicating with the inner optical path of the end portion for guiding the laser beam, an opening formed on a side of a tip of the pipe and communicating with the inner optical path of the pipe, and a mirror disposed in the opening side of the inner optical path of the pipe for discharging the laser beam having been guided through the inner optical paths to outside through the opening;
    a rotary knob rotatably attached to a bent end portion side of the grip portion so that the rotary knob is rotated with a finger or fingers of the operator's hand holding the grip portion; and
    a rotation transmitting mechanism, disposed between the rotary knob and the laser guiding pipe, for transmitting rotation of the rotary knob to the laser guiding pipe to pivot the pipe about an axis of the pipe so as to change an irradiation direction of the laser beam to be discharged through the opening.

2. A laser treatment apparatus including the laser hand-piece according to claim 1.

3. The laser hand-piece according to claim 1, wherein the rotation transmitting mechanism includes a flexibly bendable member for transmitting the rotation of the rotary knob to the laser guiding pipe, the flexibly bendable member being disposed covering the end portion of the main body.

4. The laser hand-piece according to claim 3, wherein the flexibly bendable member has an integral configuration with the rotary knob.

5. The laser hand-piece according to claim 3, wherein the flexibly bendable member is made from hard rubber.

6. The laser hand-piece according to claim 3, wherein the flexibly bendable member has a bellows portion.

7. A laser hand-piece of a bent-type, for irradiating a treatment laser beam to a part to be treated, including:
    a main body including a bent end portion and a grip portion to be held by an operator's hand, the end and grip portions each having an inner optical path communicating with each other for guiding the laser beam;
    a laser guiding pipe pivotably mounted on the end portion of the main body and provided with an inner optical path communicating with the inner optical path of the end portion for guiding the laser beam, an opening formed on a side of a tip of the pipe and communicating with the inner optical path of the pipe, and a mirror disposed in the opening side of the inner optical path of the pipe for discharging the laser beam having been guided through the inner optical paths to outside through the opening;
    a rotary knob rotatably attached to a bent end portion side of the grip portion so that the rotary knob is rotated with a finger or fingers of the operator's hand holding the grip portion;
    a rotation transmitting mechanism, disposed between the rotary knob and the laser guiding pipe, for transmitting rotation of the rotary knob to the laser guiding pipe to pivot the pipe about an axis of the pipe so as to change an irradiation direction of the laser beam to be discharged through the opening, the rotation transmitting mechanism including a rotation preventing mechanism for stopping the rotation of the rotary knob at a predetermined rotational position.

8. The laser hand-piece according to claim 1, wherein the laser guiding pipe is removably mounted on the end portion of the main body.

* * * * *